US006806290B2

(12) United States Patent
Pflaum et al.

(10) Patent No.: US 6,806,290 B2
(45) Date of Patent: *Oct. 19, 2004

(54) STABILIZED PHARMACEUTICALLY EFFECTIVE COMPOSITION AND PHARMACEUTICAL FORMULATION COMPRISING THE SAME

(75) Inventors: Zlatko Pflaum, Domzale (SI); Janez Kerc, Ljubljana (SI)

(73) Assignee: LEK Pharmaceuticals d.d., Ljubljana (SI)

(*) Notice: Subject to any disclaimer, the term of this patent is extended or adjusted under 35 U.S.C. 154(b) by 226 days.

This patent is subject to a terminal disclaimer.

(21) Appl. No.: 10/298,187

(22) Filed: Nov. 15, 2002

(65) Prior Publication Data

US 2003/0109584 A1 Jun. 12, 2003

Related U.S. Application Data

(63) Continuation-in-part of application No. 09/591,322, filed on Jun. 9, 2000, now Pat. No. 6,531,507.

(51) Int. Cl.$^7$ .................. A61K 31/225; A61K 31/40
(52) U.S. Cl. .................. 514/547; 514/429; 514/423
(58) Field of Search .................. 514/547, 429, 514/423

(56) References Cited

U.S. PATENT DOCUMENTS

| 5,798,375 A | 8/1998 | Tsujita et al. ............... 514/369 |
| 6,531,507 B1 * | 3/2003 | Pflaum et al. ............... 514/547 |

FOREIGN PATENT DOCUMENTS

| EP | 0 336 298 A1 | 10/1989 | ............ A61K/31/19 |
| EP | 0 336 298 B1 | 10/1989 | ............ A61K/31/19 |
| EP | 0 547 000 A1 | 6/1993 | ............ A61K/31/19 |
| GB | 2055 100 A | 2/1981 | ............ C07C/69/00 |
| WO | WO 94/16693 | 8/1994 | ............ A61K/31/40 |
| WO | WO 97/03959 | 2/1997 | ............ C07D/207/34 |
| WO | WO 97/23200 | 7/1997 | ............ A61K/9/20 |
| WO | WO 00/17150 | 3/2000 | ............ C07C/69/01 |
| WO | WO 00/35425 | 6/2000 | ............ A61K/9/22 |

OTHER PUBLICATIONS

PCT/IB 99/01749 International Search Report.
PCT/IB 00/00773 International Search Report.

* cited by examiner

Primary Examiner—Sreeni Padmanabhan
Assistant Examiner—Donna Jagoe
(74) Attorney, Agent, or Firm—Bromberg & Sunstein LLP

(57) ABSTRACT

Lovastatin, pravastatin, simvastatin, mevastatin, atorvastatin, and derivatives and analogs thereof are known as HMG-CoA reductase inhibitors and are used as antihypercholesterolemic agents. The majority of them are produced by fermentation using microorganisms of different species identified as species belonging to Aspergillus, Monascus, Nocardia, Amycolatopsis, Mucor or Penicillium genus, and some are obtained by treating the fermentation products using the methods of chemical synthesis or they are the products of total chemical synthesis. The aforementioned active substances may be destabilized by the environmental factors, their degradation may also be accelerated by interactions with other pharmaceutical ingredients, such as fillers, binders, lubricants, glidants and disintegrating agents, therefore the pharmaceutical ingredients and the process for preparation of the pharmaceutical formulation should be meticulously chosen to avoid the aforementioned undesired interactions and reactions. The present invention relates to a HMG-CoA reductase inhibitor which is stabilized by forming a homogeneous composition with a buffering substance or a basifying substance. This homogeneous composition is suitably used as the active substance in a pharmaceutical formulation for the treatment of hypercholesterolemia and hyperlipidemia.

43 Claims, 4 Drawing Sheets

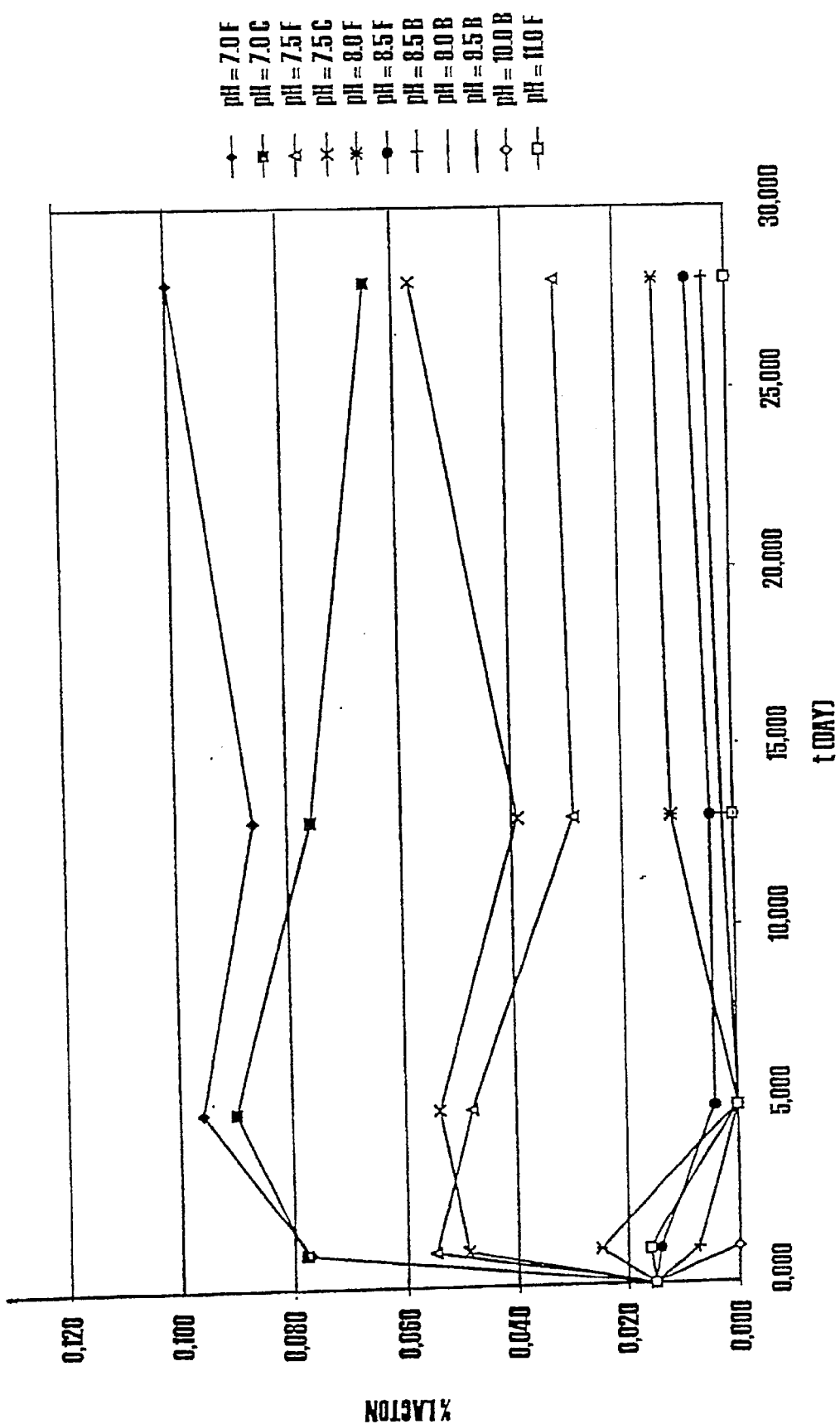

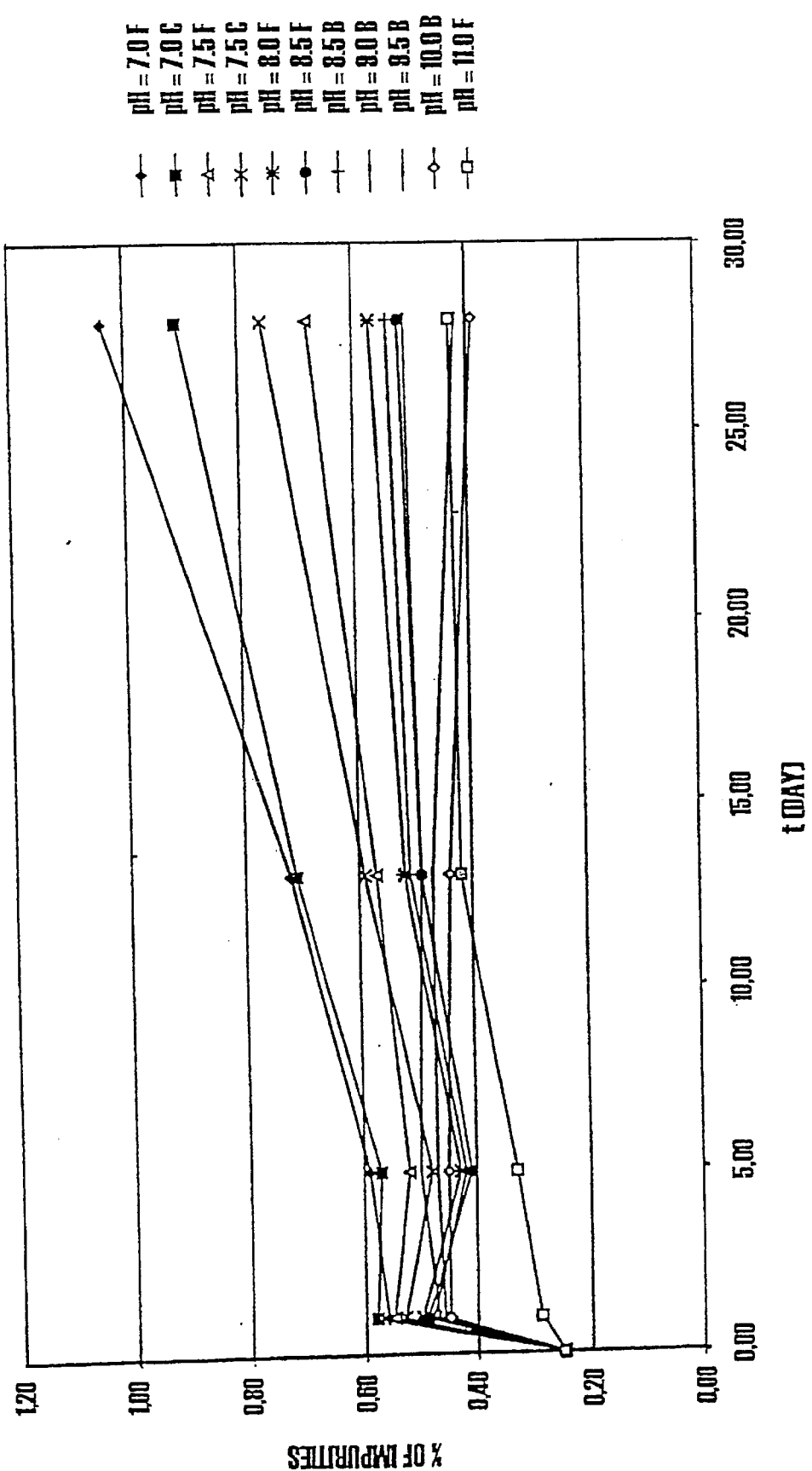

US 6,806,290 B2

STABILIZED PHARMACEUTICALLY EFFECTIVE COMPOSITION AND PHARMACEUTICAL FORMULATION COMPRISING THE SAME

CROSS REFERENCE TO RELATED APPLICATIONS

This application is a continuation-in-part of U.S. application Ser. No. 09/591,322 filed on Jun. 9, 2000, which is now U.S. Pat. No. 6,531,507. Its disclosure is incorporated herein by reference.

FIELD OF THE INVENTION

The present invention relates to a newly stabilized HMG-CoA reductase inhibitor which is used in a pharmaceutical formulation being particularly suitable for the treatment of hypercholesterolemia and hyperlipidemia.

More precisely, the present invention relates to a stabilized and very homogeneous composition mixture comprising a HMG-CoA reductase inhibitor, such as atorvastatin, pravastatin, fluvastatin and cerivastatin, or pharmaceutically active salts thereof, as well as solid pharmaceutical formulations containing the aforementioned homogeneous composition mixture as an active substance. The present invention relates more particularly to a stabilized and very homogeneous composition mixture comprising a HMG CoA reductase inhibitor or its pharmaceutically active salts, as well as solid pharmaceutical formulations containing the aforementioned homogeneous composition mixture as an active substance and which has increased stability as determined by a small change of its pH value and lactone content under storage and/or handling conditions. The present invention relates most particularly to a stabilized and very homogeneous composition mixture comprising pravastatin or its pharmaceutically active salts, as well as solid pharmaceutical formulations containing the aforementioned homogeneous composition mixture as an active substance and which has increased stability as determined by a small change of its pH value and lactone content under storage and/or handling conditions.

BACKGROUND OF THE INVENTION

Lovastatin, pravastatin, simvastatin, mevastatin, atorvastatin, fluvastatin and cerivastatin, derivatives and analogs thereof are known as HMG-CoA reductase inhibitors and are used as antihypercholesterolemic agents. The majority of them are produced by fermentation using microorganisms of different species identified as species belonging to Aspergillus, Monascus, Nocardia, Amycolatopsis, Mucor or Penicillium genus. Some are obtained by treating the fermentation products using the methods of chemical synthesis like simvastatin or they are the products of total chemical synthesis like fluvastatin, atorvastatin and cerivastatin.

The purity of the active substance is an important factor for manufacturing a safe and effective pharmaceutical formulation. Maximum possible purity of the product is of particular importance if the pharmaceutical product must be taken on a longer term basis in the treatment or prevention of high cholesterol levels in blood. Accumulation of impurities from drugs of a lower level of purity may cause a variety of side effects during treatment. Besides impurities that cannot be completely eliminated in the process of preparation of the active substance degradation products occurring by subjecting the final pharmaceutical formulation to various environmental factors such as temperature, moisture, low pH, carbon dioxide from the air and light, may also impose a significant problem. HMG-CoA reductase inhibitors occurring in the form of salts in the final pharmaceutical formulation, such as atorvastatin, pravastatin, fluvastatin and cerivastatin, are particularly sensitive to an acidic environment in which hydroxy acids are degraded into a lactone.

Apart from the fact that the aforementioned active substance may be destabilized by the environmental factors, their degradation may also be accelerated by interactions with other pharmaceutical ingredients, such as fillers, binders, lubricants, glidants and disintegrating agents.

Therefore, the pharmaceutical ingredients and the process for preparation of the pharmaceutical formulation should be meticulously chosen to avoid the aforementioned undesired interactions and reactions.

The stability of the active substance in an acidic environment is one of the major problems in the case of statins in the form of salts. One of possible solutions of the aforementioned problem is described in EP 0 336 298, U.S. Pat. No. 5,030,447 and U.S. Pat. No. 5,180,589, disclosing a stable pharmaceutical formulation for pravastatin. The essence of the formulation is to maintain an alkaline environment so that the aqueous dispersion of the pharmaceutical formulation reaches a pH above 9, preferably about 10. In addition to the active substance pravastatin, the composition of the invention includes a basifying agent, such as magnesium oxide, which imparts a pH to an aqueous dispersion of the aforementioned formulation above 9. In view of the stability of the active substance such a formulation is effective. These references disclose the pharmaceutical composition in a tablet form being subjected to a stability study at 60° C. or 40° C. and 75% relative humidity for a period of up to 2 or several months, wherein no lactone formation was observed. However, the local alkaline environment occurring at the site of dissolution of the pharmaceutical formulation may have a negative impact on the gastric mucosa with its normally acidic environment, especially since a relatively high amount of basifying agent is necessary to ensure acceptable stability. This negative impact may be particularly evident for patients with a damaged gastric mucous membrane where the mucosa per se is not able to create a sufficient acidic environment inside the stomach for normal digestive functioning. It is particularly important in chronic therapies as in the case of prophylaxis or treatment with HMG-CoA reductase inhibitors.

Another approach for providing a stable pharmaceutical formulation is described in the present Applicant's earlier PCT application No. PCT/IB99/01749 with publication No. WO 00/35425, which discloses stabilization of an HMG CoA reductase inhibitor in a solid formulation with a buffering agent. Among the HMG CoA reductase inhibitors disclosed are pravastatin, atorvastatin, fluvastatin and cerivastatin, which are said and known to be particularly sensitive to an acidic environment. The pH of the active substance is thus adjusted within the range from 7 to 11 in an aqueous medium in the course of preparing the salt of the HMG CoA reductase inhibitor from the acid form and an alkaline substance and additionally the active substance is further mixed with an appropriate buffering agent. The active substance contains small amounts of a buffering agent, preferably less than 1%, more preferably 0.1 to 0.5% and most preferably approximately 0.3% based on the weight of the active substance.

Among the buffering agents used for stabilizing the active substance are disclosed carbonate buffer or phosphate buffer, such as sodium carbonate. In addition to this the final pharmaceutical formulation of active substance and other excipients is further stabilized by a further addition of a buffering agent so as to provide a pH lower than 9 of a pharmaceutical formulation in an aqueous medium. This is achieved by addition of 20%, more preferably by 10% per weight based on the total weight of the tablet. Among the suitable buffering agents to stabilize such a pharmaceutical formulations are disclosed sodium and magnesium carbonate, sodium phosphate, sodium and potassium citrate, dibasic sodium phosphate, calcium carbonate, hydrogen phosphate, phosphate, sulfate, sodium ascorbinate, benzoate, sodium or potassium hydrogen carbonate, lauryl sulfate or mixtures thereof.

Stable pharmaceutical compositions containing 7-substituted-3,5-dihydroxyheptanoic acids or 7-substituted-3,5-dihydroxyheptenoic acids are disclosed in WO 0176566 and US 20020035142. Among 7-substituted-3,5-dihydroxyheptanoic acids are disclosed pravastatin and atorvastatin and their pharmaceutically acceptable acid salts. These compounds in such stable pharmaceutical compositions are stabilized by a stabilizing effective amount of at least one amido-group containing polymeric compound or at least one amino-group containing polymeric compound or a combination thereof, wherein said stabilized pharmaceutical composition does not contain a stabilizing effective amount of another stabilizer or a combination of other stabilizers. Disclosed is also a lactone content of such compositions in tablet form with other excipients upon subjecting the tablet compositions to a PVDC/PVC blister stability study at 40° C./75% relative humidity for up to 3 or 6 months. Pravastatin sodium compositions disclosed have lactone content based on the weight percentage at time 0 of from 0.0% to 0.6% depending on the composition, excipients and active agent and after 1 month study of from 0.2% to 1.5% depending on the composition, excipients and active agent. Disclosed pravastatin sodium formulations have lactone content of 0.0% at time 0 and of from 0.2% to 1.5% after 1 month study depending on the composition and its excipients.

Crystalline forms of atorvastatin hemi calcium salt are disclosed in U.S. Pat. No. 5,969,156 and WO 9703959, which are produced from atorvastatin lactone by help of sodium hydroxide to form a ring-opened sodium salt of atorvastatin and by help of calcium acetate hemihydrate to convert the thus obtained sodium salt into a form of a calcium salt of atorvastatin. The two agents sodium hydroxide and calcium acetate hemihydrate are here used for production of crystalline atorvastatin.

Known and disclosed stabilized compositions of HMG CoA reductase inhibitors are compositions, which are mixtures of a respective HMG CoA reductase inhibitor and more than one pharmaceutical excipient or of a respective HMG CoA reductase inhibitor and a basifying agent selected from the group of inorganic alkaline and alkaline earth metal oxides and hydroxides.

An active substance of the pravastatin sodium with a certain lactone content, namely substantially pure pravastatin sodium or pravastatin sodium with lactone content of less than 0.5% or less than 0.2%, is disclosed in WO 0230415 and US 20020082295, wherein such pravastatin sodium is obtained by a specified process for recovering pravastatin sodium from a fermentation broth in high purity, comprising a specified sequence of steps. The specified steps are forming an enriched organic solution of pravastatin, precipitating pravastatin as ammonium salt, purifying the ammonium salt by recrystallization, transposing the ammonium salt to pravastatin sodium and isolating pravastatin substantially free of pravastatin lactone and epipravastatin. This document does not teach about stabilizing of this active substance or its composition.

There continues to be the need to prepare a stabilized active substance of HMG-CoA reductase inhibitor or its pharmaceutically active salts, which will provide pH values and lactone contents that will remain stable under normal storage and/or handling conditions along the time and the change of which will be small under stressed storage conditions along the time. Such an active substance is provided in accordance with the present invention.

SUMMARY OF THE INVENTION

It is an object of the present invention to provide a pharmaceutical formulation containing as an active substance a HMG-CoA reductase inhibitor which exerts an excellent stability while avoiding the aforementioned disadvantages.

It is a particular object to provide a stabilized active substance as such, i.e. before being formulated into the pharmaceutical formulation, where the HMG-CoA reductase inhibitor is precautionary protected from being degraded.

It is a further object to provide a process for the preparation of a stabilized HMG-CoA reductase inhibitor which exerts an excellent stability while avoiding the aforementioned disadvantages. It is also an object of this invention to prepare a stabilized active substance of HMG-CoA reductase inhibitor or its pharmaceutically active salts, which will provide pH values and lactone contents that will remain stable under normal storage and/or handling conditions along the time and the change of which will be small under stress storage conditions along the time.

These and further objects are accomplished by the present invention.

According to the present invention, there is provided a composition comprising a homogeneous mixture of a HMG-CoA reductase inhibitor with a buffering substance or a basifying substance, which composition has been obtained by co-crystallization and/or co-precipitation of said HMG-CoA reductase inhibitor and said buffering substance or basifying substance.

By means of co-crystallization and/or co-precipitation, the obtained dried HMG-CoA reductase inhibitor compound itself is mixed with the buffering substance or the basifying substance in a very homogeneous and finely distributed form. It is believed that the buffering substance or the basifying substance is finely distributed around the HMG-CoA reductase inhibitor crystals, thus forming a kind of protective "microenvironment".

The protective effect in such a stabilized active substance is much more efficient than in the case of merely mixing or granulating starting powders of active substance and excipients of the pharmaceutical formulation, even in a wet process, as performed in EP 0 336 298 A. Moreover, since already the active substance HMG-CoA reductase inhibitor as such (in bulk) is efficiently protected against deleterious environmental factors due to the excellent homogeneous distribution with the buffering substance or the basifying substance, the active substance HMG-CoA reductase inhibitor can be handled more conveniently and stably stored as such, if desired, before being added to the pharmaceutical formulation. In particular, the homogeneous composition of the active substance according to the present invention is highly resistant to the negative effect of carbon dioxide and moisture from the air, and a much better protection against low pH conditions is achieved when the composition containing the active substance HMG-CoA reductase inhibitor is incorporated as the active substance into the final pharmaceutical formulation.

Accordingly, the present invention also makes available a newly stabilized pharmaceutical formulation comprising the aforementioned specific composition as the active substance.

According to the present invention, there is further provided a process for preparing a stabilized HMG-CoA reductase inhibitor which comprises the step of crystallization and/or precipitation of the HMG-CoA reductase inhibitor with the buffering substance or the basifying substance.

BRIEF DESCRIPTION OF THE DRAWINGS

FIG. 2 is a diagram which shows the occurrence of pravastatin in lactone form when pravastatin was dissolved in different buffers with the pH in a range between 7 and 11 (F=phosphate, C=citrate, B=borate).

FIG. 3 is a diagram which shows the formation of different degradation products (impurities) when pravastatin was dissolved in different buffers with the pH in a range between 7 and 11 (F=phosphate, C=citrate, B=borate).

DETAILED DESCRIPTION OF SPECIFIC EMBODIMENTS

Definitions

Figure 1A:
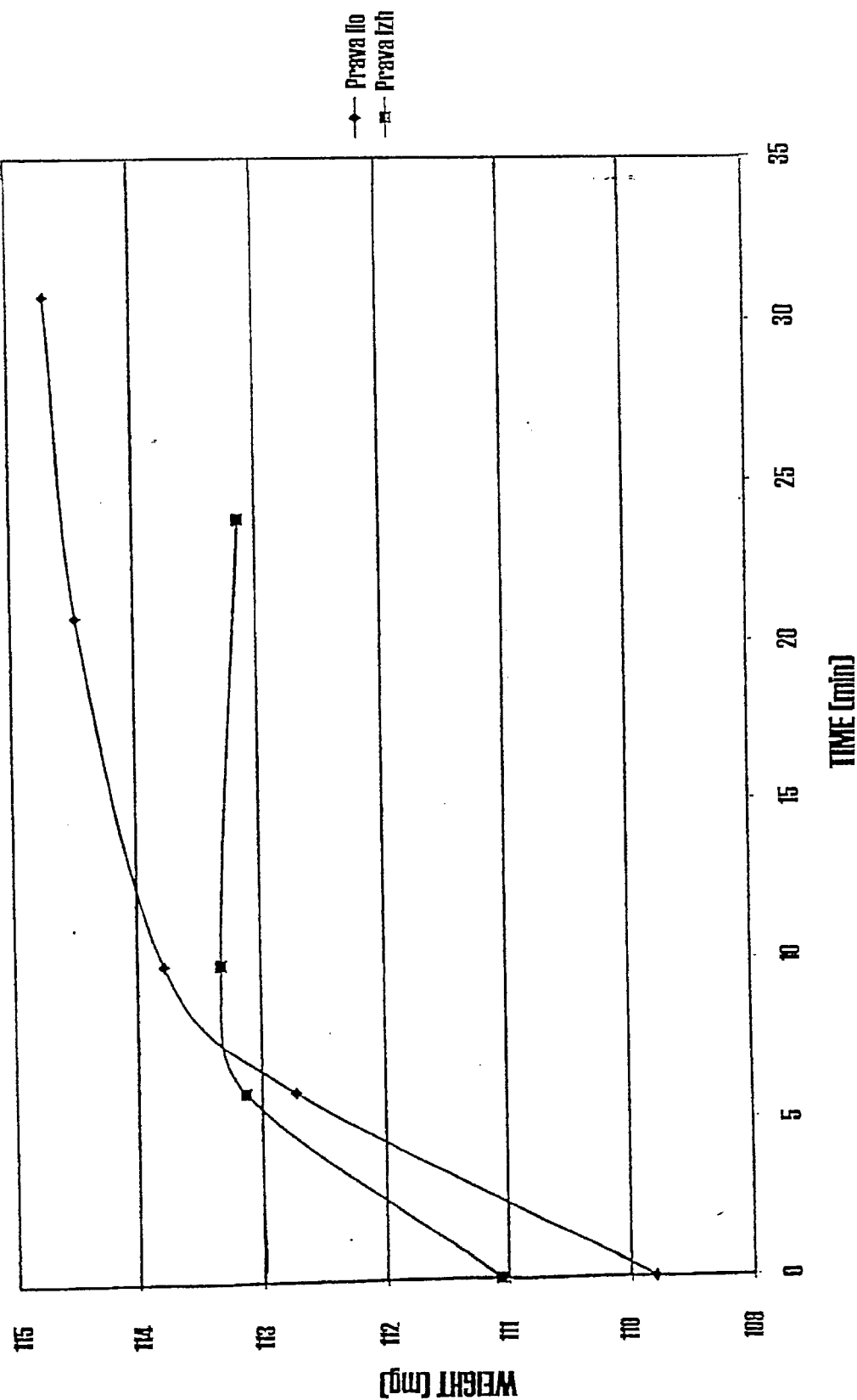
FIG. 1A is a diagram which shows the growth of weight of a sample of pravastatin in crystal form and a sample of lyophilized pravastatin when exposed to air moisture.

The term "in a very homogeneous and finely distributed form" within the scope of this invention means such a fine distribution of a buffering substance or a basifying substance, which is achieved and obtained by simultaneous co-crystallization and/or co-precipitation of an active substance HMG CoA reductase inhibitor and a buffering substance or a basifying substance, and in which the buffering substance or the basifying substance is finely distributed around the crystals of the active substance HMG CoA reductase inhibitor and thus forms a protective microenvironment.

Within the scope of this invention the term "an active substance" is interchangeable with and has the same meaning as the term an active agent or raw HMG CoA reductase inhibitor or raw crystals of HMG CoA reductase inhibitor or raw crystals of pravastatin, of atorvastatin, of fluvastatin or of cerivastatin or raw active agent or raw active substance and means an active substance HMG CoA reductase inhibitor and more particularly one of the HMG CoA reductase inhibitors selected from the group consisting of pravastatin, atorvastatin, fluvastatin, cerivastatin and pharmaceutically acceptable salts thereof.

Within the scope of this invention the term "a stabilized active substance" or "a stabilized active agent" means an active substance or an active agent HMG CoA reductase inhibitor obtained according to this invention and which has improved stability. More particularly the term a stabilized active substance or a stabilized active agent or an active substance or an active agent HMG CoA reductase inhibitor obtained according to this invention further means a composition comprising a homogeneous mixture of a HMG CoA reductase inhibitor with a buffering substance or a basifying substance in a finely distributed form, obtained by co-crystallization and/or co-precipitation of said HMG CoA reductase inhibitor and said buffering substance or basifying substance.

Within the scope of this invention the term "which will provide a pH value" means a pH value that is measured in an aqueous solution or dispersion of an active substance or of a mixture of the active substance with the buffering substance or of a stabilized active substance according to this invention or of a pharmaceutical formulation or of a stabilized pharmaceutical formulation of an active substance obtained according to this invention. The concentration of such an aqueous solution or dispersion is 1% or 5%. The measurement procedure is described in Examples 1–11.

Within the scope of this invention the term "lactone content" means percentage (%) of lactone that is contained based on the total weight of the substance or mixture in the active substance or in the mixture of the active substance with the buffering substance or in the stabilized active substance obtained according to this invention and that is determined by HPLC method as described in Examples 1–11.

Within the scope of this invention the term "normal storage conditions" means storage conditions of 40+–2° C. and 75+–5% relative humidity and storage conditions of 25+–2° C. and 60+–5% relative humidity in a thermostatically controlled chamber.

Within the scope of this invention the term "stress storage conditions" means storage conditions in CO2 atmosphere at 40° C. in a thermostatically controlled chamber.

Within the scope of this invention the term "handling conditions" means handling of active substance or stabilized active substance in normal atmosphere (at room temperature and air atmosphere) at which the active substance or stabilized active substance is processed into a pharmaceutical formulation.

In the inventor's investigations, it was found that there are three major reasons for instability problems in case of a pharmaceutical formulation containing an active substance and in case of a bulk active substance.

Figure 1B:
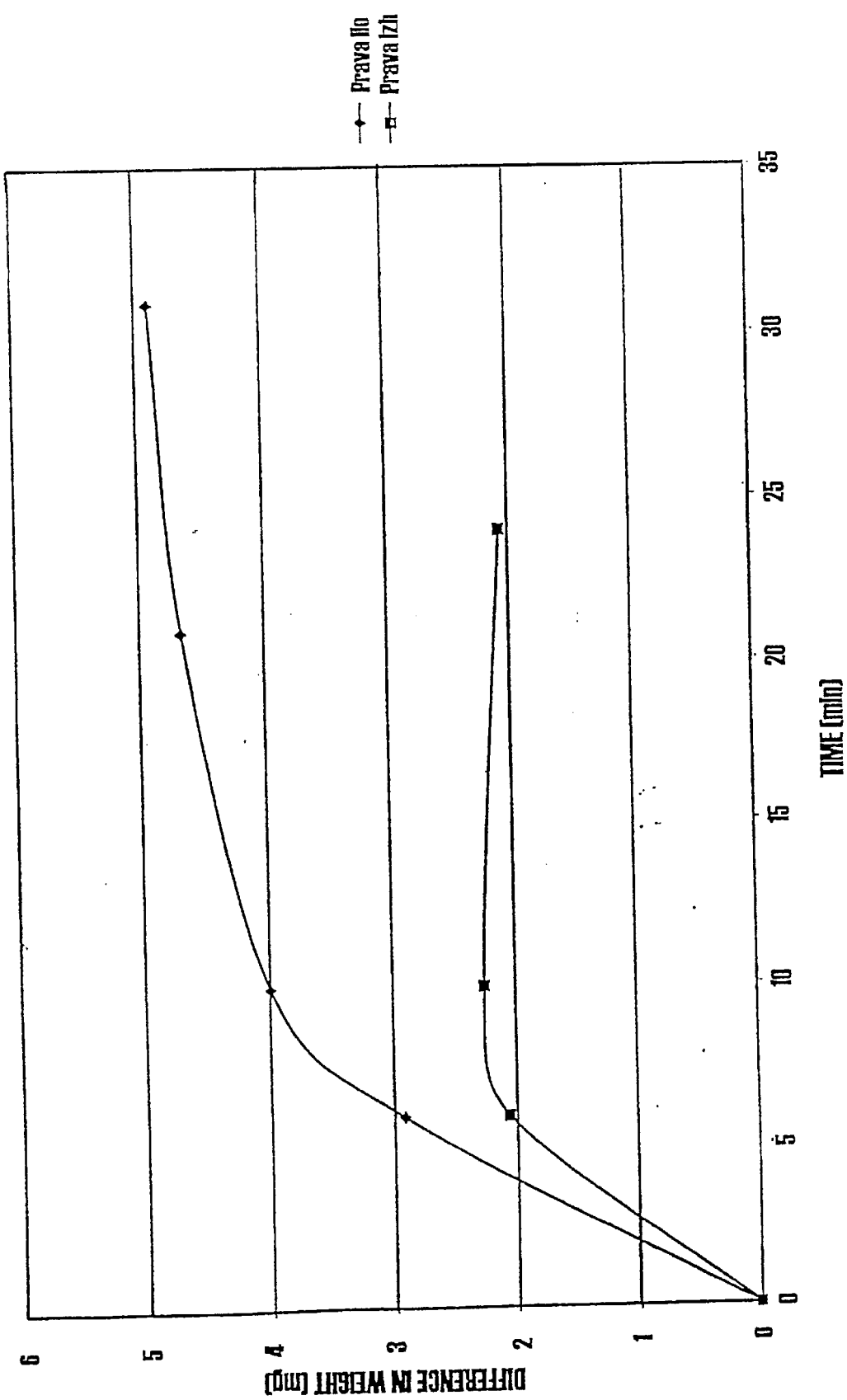
FIG. 1B shows the corresponding difference in the starting weight and the weight in time.

First, the active substance as such is very hygroscopic and it is impossible to remove all water from it. This is illustrated by the following experiment: 111.07 mg of pravastatin in crystal form (prava izh) and 109.8 mg of lyophilized pravastatin (prava lio) were exposed to air moisture. Their weights were measured in different time intervals. The growth of weight of both samples and the difference in the starting weight and the weight in time are illustrated in FIGS. 1A and 1B.

Another observation was that carbon dioxide from the air may irreversibly and reversibly bind to the active substance and can cause a drop of pH. This is illustrated by the following experiment: 5 g of pravastatin sodium were dissolved in 30 ml of methanol, the pH was adjusted to 10 with 3% aqueous solution of NaOH. 400 ml of ethylacetate were added and the crystals of pravastatin sodium were formed. Crystals were filtered and dried and then put into three different atmospheres: normal air, nitrogen atmosphere and carbon dioxide atmosphere. In normal air and in the nitrogen atmosphere the pH remained the same during a period of 24 hours (normal air: pH 9.2, nitrogen: pH 9.5), but in the carbon dioxide atmosphere the pH dropped in the first two minutes from 9.2 to 6.9. After 12 minutes the pH was 6.6 and after 1 hour the pH was 6.5. After that, the pH remained constant.

The third observation is that a sufficient stabilization of the active substance is already obtained at a pH of at least 7.0, but a beneficially high stability is effected at a pH of at least 8.0. We have noticed that at a pH below 8 the formation of lactone has occurred and also the amount of other impurities has increased. The presence of humidity in the air and a carbon dioxide-rich atmosphere makes the negative effect of a low pH even stronger. This is illustrated by the following experiment: Pravastatin was dissolved in different buffers with the pH in a range between 7 and 11 (F=phosphate, C=citrate, B=borate).

The occurrence of pravastatin in lactone form and the formation of different degradation products (impurities) were measured after 1, 5, 13 and 28 days. The results are shown in FIGS. 2 and 3.

In the present invention, we have surprisingly found that a sufficient stability of the active substance, which is a HMG-CoA reductase inhibitor preferably in the form of salt, can be also obtained by using a pharmaceutical formulation which does not create a marked alkaline environment in an aqueous dispersion. In order to achieve this efficiently, it is significant that the HMG-CoA reductase inhibitor is present in a homogeneous mixture by co-crystallization and/or co-precipitation with the buffering substance or the basifying substance in the composition according to the present invention, before the mixed composition is incorporated into the pharmaceutical formulation as the active substance. The composition of the present invention, which is the pharmaceutically active substance, may essentially consist only of said homogeneous co-crystallized and/or co-precipitated HMG-CoA reductase inhibitor and buffering substance or basifying substance, but may contain further components and additives as desired.

Another surprising finding was that a sufficient stability of a HMG-CoA reductase inhibitor in the form of a salt in bulk can be obtained even when amount of the buffering substance or the basifying substance crystallized and/or precipitated with the HMG-CoA reductase inhibitor is low.

In the conventional stabilization concept described in EP-A-0 336 298, the basifying substance is added to the pharmaceutical formulation in an amount from 1 to 75 wt.-%, and in the Examples the weight ratio of the basifying substance relative to pravastatin is from 33 to 500%.

According to the present invention, a protective effect can be achieved at lower ratios of the buffering substance or the basifying substance, such as below 30 wt % while this ratio is preferably 10 wt.-% or less, more preferably 5 wt.-% or less and in particular 1 wt.-% or less, relative to the amount of co-crystallized or co-precipitated HMG-CoA reductase inhibitor. The lower limit mainly depends on the environmental conditions and the kind and amounts of other components to be used for the pharmaceutical formulation, but an amount of at least 0.05 or 0.1 wt.-% of the buffering substance or the basifying substance, relative to the amount of HMG-CoA reductase inhibitor, is generally sufficient to provide a desired protective effect. Such an addition of small amounts of buffering substances or basifying substances avoids the negative effect of water already present in the bulk substance and of moisture from the air, avoids the negative effect of low pH caused by other ingredients which will be co-admixed to the pharmaceutical formulation, and avoids the possible lowering of the pH caused by carbon dioxide.

Accordingly, the active substance and the pharmaceutical formulation according to the present invention were designed to avoid the negative effect of the water present in the bulk substance and in the pharmaceutical formulation, to avoid the negative effect of low pH which can be caused by other ingredients of the pharmaceutical formulation and to avoid possible lowering of the pH caused by carbon dioxide.

Furthermore, we have recognized that the protecting effect, especially the resistance against the negative effect of carbon dioxide, is better when the buffering substance or the basifying substance is co-crystallized and/or co-precipitated rather than merely admixed by mixing, milling or granulating, which is assumed to be attributable to a more homogeneous, fine distribution in the composition according to the present invention. Accordingly, a corresponding stabilizing effect can be achieved with lower amounts of buffering substance or basifying substance.

We have surprisingly found that active substance HMG CoA reductase inhibitor, co-crystallized and/or co-precipitated with the buffering substance or the basifying substance according to this invention, has higher stability than the raw active substance (alone—without the basifying or the buffering substance) and also higher than a simple mixture of the raw active substance with the buffering substance or the basifying substance, even though the amounts of the basifying or the buffering substance present are higher than in the stabilized active substance according to this invention.

Under the stress storage and/or handling conditions of $CO_2$ atmosphere at 40° C. content of the lactone form of the active substance HMG CoA reductase inhibitor increases by the time of the storage and the rise of such lactone content is the lowest and the slowest in the sample of the stabilized active substance produced according to this invention, even though the amount of the basifying or the buffering substance added is small (e.g. only 0.2% wt) in comparison to samples of mixtures with the same small (e.g. 0.2% wt) or even higher content of the basifying or the buffering substance in a mixture with the active substance. This is even more surprising when pH values of the stabilized active substance and of such mixtures are compared.

Values of pH are decreasing by the storage time under stress conditions of $CO_2$ atmosphere. When comparing the pH values and the lactone content the stabilized active substance according to this invention and simple mixtures of the raw active substance with the buffering or the basifying substance, their lactone content differs: the former has lower lactone content and the latter has higher and even to about two times higher lactone content.

This surprisingly shows that the stabilized active substance according to this invention has higher stability than simple mixtures of the active substance with the buffering substance or the basifying substance.

Thus, it is possible to mix HMG-CoA reductase inhibitor with other ingredients of the pharmaceutical formulation without fear that a degradation can be caused by the contact of HMG-CoA reductase inhibitor with acidic ingredients, because a microenvironment of HMG-CoA reductase inhibitor is effectively made slightly basic or markedly basic due to the addition of small amounts of a buffering substance or basifying substance. This addition of a buffering substance or basifying substance is also important for an easier handling of the HMG-CoA reductase inhibitor bulk composition without special requirements for a carbon dioxide free atmosphere.

Further, we have found that for the stability and digestibility of a pharmaceutical formulation both the pH generated by the formulation in an aqueous medium (usually being a dispersion) and the pH of the active substance (i.e. the HMG-CoA reductase inhibitor-containing composition alone) preferably should be adjusted.

The most acceptable stability of the active substance in the formulations is obtained with the above composition, as the active substance, which is capable of providing a pH in the range from 7 to 12 and preferably from 8 to 11. The pH value is the one which is obtained when the pH of an aqueous medium containing said composition would be measured. In the stable pharmaceutical formulation according to the present invention, the basic pH of the active substance has a minimal influence on the pH of the formulation. By creating locally an environment around the active substance which affords the best stability for the active substance, the potential of negative impact of other ingredients of the composition of the pharmaceutical formulation is reduced, and possible reactions among the active substance and the rest of the ingredients of the composition of the pharmaceutical formulation are also less favored. Accordingly, the specific composition or active substance is maintained in a stable form when an active substance which is capable of providing a pH in an aqueous medium in the range from 7 to 12 and preferably in the range from 8 to 11 is added to the pharmaceutical formulation.

The HMG-CoA reductase inhibitor used for obtaining the specific composition or active substance of the present invention generally is in the form of a salt and may be selected from the group consisting of pravastatin, atorvastatin, fluvastatin, cerivastatin. Since the stabilizing effect becomes particularly pronounced in these cases, the HMG-CoA reductase inhibitor is preferably a calcium salt of atorvastatin (atorvastatin Ca) and most preferably a sodium salt of pravastatin (pravastatin Na).

Nonetheless, stability can be improved in accordance with the present invention also in the case of other HMG-CoA reductase inhibitors.

A process suitable for preparing the aforementioned specific composition including the stabilized HMG-CoA reductase inhibitor will now be further described. The characteristic step is the crystallization and/or precipitation of both the HMG-CoA reductase inhibitor and the buffering substance or basifying substance from the same medium. This step may be performed as the final step in the course of conventionally isolating and purifying the HMG-CoA reductase inhibitor, but it may also be performed by using an already isolated HMG-CoA reductase inhibitor which suitably has a (HPLC) purity of at least 98%, preferably of at least 99.5%. First, a solution or dispersion of the HMG-CoA reductase inhibitor and the buffering substance or basifying substance is provided. A common solvent or medium may be used for providing this solution or dispersion, for example low alkyl alcohols such as methanol, ethanol, propanol and isopropyl alcohol, low alkyl ketones such as acetone and methyl ethyl ketone, low alkyl glycol ethers such as methyl glycol, ethyl glycol, propyl glycol and ethyldiglycol, and dipolar aprotic solvents such as N,N-dimethyl-formamide (DMF), N,N-dimethylacetamide (DMA) and dimethyl sulfoxide (DMSO), including mixtures of these solvents.

Acetone and low alkyl alcohols such as methanol are preferred. Theh, an organic solvent, in which the compounds are less or hardly soluble or insoluble, is added in order to allow the HMG-CoA reductase inhibitor and the buffering substance or basifying substance to crystallize and/or precipitate together. Examples for the organic solvent include: higher alkyl alcohols such as butanol, isobutanolamyl alcohol, hexanol, 2-ethylhexanol, benzyl alcohol and cyclohexanol, higher alkyl ketones such as methylbutyl ketone, methyl isobutyl ketone and cyclohexanone, esters such as methyl acetate, ethyl acetate, n-propyl (and isopropyl) acetate, n-butyl (and iso-butyl or sec-butyl) acetate and amyl acetate, ethers such as diethyl ether and diisopropyl ether, chlorinated hydrocarbons such as methylene chloride and chloroform, acetonitrile and the like, including mixtures of these solvents. Ethyl acetate is particularly preferred as the organic solvent.

The pH of the composition (active substance) is adjusted, preferably within the above specified range, by means of the co-crystallized or co-precipitated buffering substance or basifying substance in the aforementioned amounts.

The buffering substance or agent is suitable selected from the group consisting of salts of inorganic acids, salts of organic bases or salts of organic acids. Examples of salts of inorganic acids include sodium or potassium citrate, sodium or potassium phosphate or hydrogenphosphate, dibasic sodium phosphate, sodium, potassium, magnesium or calcium carbonate or hydrogen carbonate, sulphate, or mixtures of such buffering agents, or the like; carbonate buffer or phosphate buffer, such as sodium carbonate of sodium phosphate, being preferred. Examples for salts of organic bases include aminoguanidine carbonate or hydrogen carbonate, guanidine carbonate or hydrogen carbonate, succinimide carbonate or hydrogen carbonate, 1-adamantil amine carbonate or hydrogen carbonate, N,N'-bis(2-hydroxyethyl) ethylendiamine carbonate or hydrogen carbonate, tris (hydroxymethyl) aminometan carbonate or hydrogen carbonate, D(-)-N-Methylglucamine carbonate or hydrogen carbonate, or the like. Examples for salts of organic acids include potassium or sodium salts of acetic acid, citric acid, lactic acid, ascorbic acid, maleic acid, phenyl acetic acid, benzoic acid, lauryl sulphuric acid, or the like.

The basifying substance or agent is suitable selected from the group consisting of metal oxides, inorganic bases, organic bases and organic acids with basic character. Examples of metal oxides include magnesium oxide and aluminum oxide. Examples of inorganic bases include alkali metal hydroxide such as sodium hydroxide, potassium hydroxide, alkali earth metal hydroxide such as calcium hydroxide or magnesium hydroxide. Examples of organic bases include succinimide, 1-adamantyl amine, N,N'-bis(2-hydroxyethyl) ethylendiamine, tris (hydroxymethyl) aminomethan, D(-)-N-methylglucamine, or the like. Examples of organic acids with basic character include 3-(N-morpholino) propanesulfonic acid, 4-(cyclohexyl amino)-1-butansulfonic acid, 4-(cyclohexyl amino) etansulfonic acid and the alkaline metal or alkaline earth metal salts of these acids, arginine, ornithine, lysine, or the like.

The buffering or basifying substance may also be generated in situ, for example by adding an alkali metal or alkali earth metal hydroxide to the solution and then blowing carbon dioxide into the solution until a desired pH is adjusted.

The composition prepared according to this invention, which comprises a homogeneous mixture of the HMG CoA reductase inhibitor with the buffering substance or the basifying substance in the finely distributed form, obtained by co-crystallization and/or co-precipitation of said HMG CoA reductase inhibitor and said buffering substance or basifying substance has a HPLC purity of at least 98%. Preferably its HPLC purity is of at least 99.5% and more preferably of 99.6%. Such a composition further has a pH value in the range from 7 to 12 and more preferably in the range from 8 to 11. The said HMG CoA reductase inhibitor of such a composition is selected from the group consisting of pravastatin, atorvastatin, fluvastatin, cerivastatin and pharmaceutically acceptable salts thereof and is preferably a sodium salt of pravastatin (pravastatin Na) or a calcium salt of atorvastatin (atorvastatin Ca).

In one embodiment of this invention the composition comprising the homogeneous mixture of the HMG CoA reductase inhibitor with the buffering substance or the basifying substance in a finely distributed form, obtained by co-crystallization and/or co-precipitation of said HMG CoA reductase inhibitor and said buffering substance or basifying substance contains less than 0.5% wt of the lactone form of the said HMG CoA reductase inhibitor. The content of the said lactone form of the said HMG CoA reductase inhibitor is preferably below 0.2% wt, more preferably below below 0.1% wt. Further it is below 0.06% wt or below 0.05.% wt and most preferably below 0.01% wt.

Such a stabilized active substance has increased stability and the content of the lactone form of the said HMG CoA reductase inhibitor in the said e stabilized active substance does not change significantly under the storage and/or handling conditions. Preferably the content of the lactone form of the said HMG CoA reductase inhibitor in the said stabilized active substance does not change significantly under the storage and/or handling conditions and is and/or remains below 0.5% wt. More preferably such a lactone content does not change significantly under the storage and/or handling conditions and is and/or remains below 0.2% wt and even more preferably is and/or remains below 0.1% wt. Further such a lactone content does not change significantly under the storage and/or handling conditions and is and/or remains below 0.06% wt and most preferably is and/or remains below 0.01% wt. Such a stabilized active substance further has a pH value of the composition in an aqueous solution or an aqueous dispersion in the range from 7 to 12 and more preferably in the range from 8 to 11. This pH value of the composition in an aqueous solution or an aqueous dispersion further does not change significantly when the said composition is stored and/or handled under the storage and/or handling conditions and preferably remains in the range of pH from 7 to 12. More preferably a pH value of such a stabilized active substance in an aqueous solution or an aqueous dispersion does not change significantly when the said composition is stored and/or handled under the stress storage and/or handling conditions. Most preferably such a pH value does not change significantly when the said composition is stored and/or handled under the normal storage and/or handling conditions. The active agent HMG CoA reductase inhibitor in this embodiment of the invention is selected from the group consisting of pravastatin, atorvastatin, fluvastatin, cerivastatin and pharmaceutically acceptable salts thereof. More preferably the said HMG CoA reductase inhibitor is a sodium salt of pravastatin (pravastatin Na) or a calcium salt of atorvastatin (atorvastatin Ca).

In a further embodiment of this invention the stabilized active substance according to this invention is stored and/or handled under the normal storage conditions and under such conditions the content of the lactone form of the said HMG CoA reductase inhibitor in the stabilized active substance does not change significantly. Further such a lactone content does not change significantly under the normal storage and/or handling conditions and is and/or remains below 0.5% wt or even below 0.2% wt. More preferably such a lactone content does not change significantly under the normal storage or handling conditions and is and/or remains in the ranges below 0.1% wt, below 0.06% wt or below 0.05% wt. Most preferably the said lactone form of the said HMG CoA reductase inhibitor does not change significantly under the normal storage or handling conditions and is and/or remains below 0.01% wt.

In another further embodiment of this invention the stabilized active substance HMG CoA reductase inhibitor according to this invention is stored under the stress storage conditions. Under such conditions the content of the lactone form of the said HMG CoA reductase inhibitor does not change significantly under the stress storage conditions. Preferably such a lactone content does not change significantly under the stress storage conditions and is and/or remains below 0.6% wt or below 0.5% wt. More preferably such a lactone content does not change significantly under the stress storage conditions and is and/or remains in the ranges below 0.2% wt and most preferably is and/or remains below 0.1% wt.

The composition or active substance of the present invention as described above is then added to the final pharmaceutical formulation by means of an appropriate formulation process. Besides the composition (pharmaceutically active substance) of the present invention, the pharmaceutical formulation according to the present invention may further comprise at least one constituent selected from the group consisting of a filler, a binder, a disintegrating agent, a glidant, a buffering agent; optionally further comprising at least one constituent selected among coloring agents, lakes, aromas, adsorbents, film formers and plasticizers.

By means of adding further buffering or basifying substances to the formulation, it is possible to effectively improve and maintain the resistance of the final formulation against carbon dioxide by neutralizing the acidifying effect thereof. Any one of the above described buffering or basifying substances may be additionally used for the pharmaceutical formulation. In order to avoid a negative impact on the patient's gastric mucosa during the administration of the pharmaceutical formulation, it is preferable to use additional buffering substance, and to adjust the pH of the formulation, i.e. the provided pH when the pharmaceutical formulation is brought in solution or dispersion, to a range below 9, preferably below 8.5, whereas the lower limit of the pH generated by the pharmaceutical formulation suitably is 6, preferably 7. The amount of additional buffering or basifying substance may be 20 wt.-% or less, more preferably 10 wt.-% per weight or less based on the total weight of the tablet.

The pharmaceutical formulation of this invention may include, in addition to the HMG-CoA reductase inhibitor which is sensitive to a low pH environment, one or more fillers, such as microcrystalline cellulose, lactose, sugars, starches, modified starch, mannitol, sorbitol and other polyols, dextrin, dextran and maltodextrin, calcium carbonate, calcium phosphate and/or hydrogen phosphate, sulphate, one or more binders such as lactose, starches, modified starch, dextrin, dextran and maltodextrin, microcrystalline cellulose, sugars, polyethylene glycols, hydroxypropyl cellulose, hydroxypropyl methylcellulose, ethyl cellulose, hydroxyethyl cellulose, methylcellulose, carboxymethyl cellulose, gelatin, acacia gum, tragacanth, polyvinylpyrrolidone, magnesium aluminium silicate, one or more disintegrating agents such as croscarmellose sodium, cross-linked polyvinylpyrrolidone, cross-linked carboxymethyl starch, starches and microcrystalline cellulose, magnesium aluminium silicate, polyacrylin potassium, one or more different glidants such as magnesium stearate, calcium stearate, zinc stearate, calcium behenate, sodium stearyl fumarate, talc, magnesium trisilicate, stearic acid, palmitic acid, carnauba wax, silicon dioxide, one or more buffering agents such as sodium or potassium citrate, sodium phosphate, dibasic sodium phosphate, calcium carbonate, hydrogen phosphate, phosphate, sulphate, sodium or magnesium carbonate, sodium ascorbinate, benzoate, sodium or potassium hydrogen carbonate, lauryl sulphate, or mixtures of such buffering agents.

If required any, the formulation may also include surfactants and other conventional components for solid, pharmaceutical formulations such as coloring agents, lakes, aromas and adsorbents. As surfactants the following may be used: ionic surfactants, such as sodium lauryl sulphate or non-ionic surfactants such as different poloxamers (polyoxyethylene and polyoxypropylene copolymers), natural or synthesized lecithins, esters of sorbitan and fatty acids (such as Span®, manufactured by Atlas Chemie), esters of polyoxyethylenesorbitan and fatty acids (such as Tween®, manufactured by Atlas Chemie), polyoxyethylated hydrogenated castor oil (such as Cremophor®, manufactured by BASF), polyoxyethylene stearates (such as Brij®, manufactured by Atlas Chemie), dimethylpolysiloxane or any combination of the above mentioned surfactants.

If the solid pharmaceutical formulation is in the form of coated tablets, the coating may be prepared from at least one film-former such as hydroxypropyl methylcellulose, hydroxypropyl cellulose, at least from one plasticizer such as polyethylene glycols, dibutyl sebacate, triethyl citrate, and other pharmaceutical auxiliary substances conventional for film coatings, such as pigments, fillers and others.

The solid pharmaceutical formulations according to the present invention may be prepared as described below.

The mixture of the active substance, filler, binder, buffering agent, disintegrating agent and if required a surfactant and other conventional ingredients for solid pharmaceutical formulations is homogenized employing suitable mixers. Glidants and/or lubricants are added and the mixture is re-homogenized. The resulting mixture is compressed into tablets or filled into capsules. If needed, tablets can be film-coated.

The mixture of the active substance, filler, binder, buffering agent, disintegrating agent and if required a surfactant and other conventional ingredients for solid pharmaceutical formulations is homogenized employing suitable mixers, granulated with a suitable solvent such as water, ethanol, methanol, isopropyl alcohol, n-butyl alcohol, acetone, diethyl ether, ethyl acetate, isopropyl acetate, methyl acetate, dichloromethane and methanol, and mixtures of these solvents such as ethanol and acetone, methanol and acetone, dichloromethane and methanol, and the mixtures thereof. The resulting granulation is dried in suitable dryers such as standard plate dryers, fluid bed dryers, vacuum and microwave dryers. To the dried granulation, glidants and/or lubricants and if required other conventional ingredients for solid pharmaceutical formulations are added. The resulting mixture is re-homogenized and compressed into tablets or filled into capsules. Optionally, tablets are film-coated.

The present invention is illustrated but by no means limited by the following examples.

EXAMPLES

The following instrumentation was used in the Examples 1–11.

LDC HPLC System: column (30×4.6) mm Lichrospher, detector 236 nm, sample cca. 500 mg/L injector 5 µL, mobile phase A: 15% ACN, mobile phase B: 90% ACN, gradient 0': 100% A, 3,5'100% B, flow 2.8 ml/min;

pH Meter: Iskra MA 5741

(I) Stabilizing of HMG-CoA Reductase Inhibitor by Addition of Salts of Inorganic Acids Example 1
Stabilizing of Pravastatin Sodium by Addition of Sodium Carbonate Pravastatin Sodium (I-17226103B, 5 g) with chromatographic purity 99.5% and pH 7.4 (1%)/7.7 (5%) was dissolved in methanol (30 ml), sodium carbonate (10 mg, dissolved in 0.15 ml of water) was added and finally, ethylacetate (400 ml containing 2% of water) was added. After 1 hour the resulted crystals were filtered off, washed with fresh ethylacetate (50 ml) and dried at 40° C. for 6 hours in vacuo.

The chromatographic purity of resulted crystals (4.3 g) was 99.6% and pH was 9.5 (1%)/9.8 (5%).

The results of the stability measurements are shown in Table 1.

Example 2
Stabilizing of Pravastatin Sodium by Addition of Sodium Hydrogen Carbonate Pravastatin Sodium (I-17226103B, 5 g) with chromatographic purity 99.5% and pH 7.4 (1%)/7.7 (5%) was dissolved in methanol (30 ml), sodium hydrogen carbonate (10 mg, dissolved in 0.15 ml of water) was added and finally, ethylacetate (400 ml, containing 2% of water) was added. After 1 hour the resulted crystals were filtered off, washed with fresh ethylacetate (50 ml) and dried at 40° C. for 6 hours in vacuo.

The chromatographic purity of resulted crystals (4.4 g) was 99.6% and pH was 9.2 (1%)/9.6 (5%).

The results of the stability measurements are shown in Table 1.

Example 3
Stabilizing by Addition of di-Sodium Hydrogen Phosphate

Pravastatin Sodium (I-17226103B, 5 g) with chromatographic purity 99.5% and pH 7.4 (1%)/7.7 (5%) was dissolved in methanol (30 ml), di-sodium hydrogen phosphate (10 mg, dissolved in 0.15 ml of water) was added and finally, ethylacetate (400 ml, containing 2% of water) was added. After 1 hour the resulted crystals were filtered off, washed with fresh ethylacetate (50 ml) and dried at 40° C. for 6 hours in vacuo.

The chromatographic purity of resulted crystals (4.3 g) was 99.6% and pH was 8.0 (1%)/8.4 (5%).

The results of the stability measurements are shown in Table 1.

Example 4
Stabilizing with Sodium Hydroxide and Carbon Dioxide

Pravastatin Sodium (I-17226103B. 5 g) with chromatographic purity 99.5% and pH 7.4 (1%)/7.7 (5%) was dissolved in methanol (30 ml), sodium hydroxide was added to reach pH 9.5, carbon dioxide was blown into the solution to reach pH of 8.3 (equilibrium) and finally, ethylacetate (400 ml, containing 2% of water) was added. After 1 hour the resulted crystals were filtered off, washed with fresh ethylacetate (50 ml) and dried at 40° C. for 6 hours in vacuo.

The chromatographic purity of resulted crystals (4.3 g) was 99.6% and pH was 7.7 (1%)/8.3 (5%).

The results of the stability measurements are shown in Table 1.

(II) Stabilizing of Pravastatin Sodium by Addition of Salts of Organic Base

Example 5
Stabilizing by Addition of Aminoguanidine Hydrogen Carbonate

Pravastatin Sodium (I-17226103B, 5 g) with chromatographic purity 99.5% and pH 7.4 (1%)/7.7 (5%) was dissolved in methanol (30 ml), aminoguanidine hydrogen carbonate (10 mg, dissolved in 1 ml of water) was added and finally, ethylacetate (400 ml, containing 2% of water) was added. After 1 hour the resulted crystals were filtered off, washed with fresh ethylacetate (50 ml) and dried at 40° C. for 6 hours in vacuo.

The chromatographic purity of resulted crystals (4.2 g) was 99.6% and pH was 8.1 (1%)/8.8 (5%). The results of the stability measurements are shown in Table 1.

(III) Stabilizing of Pravastatin Sodium by Addition of Salts of Organic Acids

Example 6
Stabilizing by Addition of Sodium Acetate

Pravastatin Sodium (I-17226103B, 5 g) with chromatographic purity 99.5% and pH 7.4 (1%)/7.7 (5%) was dissolved in methanol (30 ml), sodium acetate (10 mg, dissolved in 0.15 ml of water) was added and finally, ethylacetate (400 ml, containing 2% of water) was added. After 1 hour the resulted crystals were filtered off, washed with fresh ethylacetate (50 ml) and dried at 40° C. for 6 hours in vacuo.

The chromatographic purity of resulted crystals (4.3 g) was 99.6% and pH was 7.9 (1%)/8.3 (5%).

The results of the stability measurements are shown in Table 1.

(IV) Stabilizing of Pravastatin Sodium by Addition of the Inorganic Base

Example 7
Stabilizing by Addition of Magnesium Oxide (or Hydroxide)

Pravastatin Sodium (I-17226103B, 5 g) with chromatographic purity 99.5% and pH 7.4 (1%)/7.7 (5%) was dissolved in methanol (30 ml), magnesium oxide (10 mg) was added and finally, ethylacetate (400 ml, containing 2% of water) was added. After 1 hour the resulted crystals were filtered off, washed with fresh ethylacetate (50 ml) and dried at 40° C. for 6 hours in vacuo.

The chromatographic purity of resulted crystals (4.3 g) was 99.6% and pH was 8.7 (1%)/9.3 (5%).

The results of the stability measurements are shown in Table 1.

(V) Stabilizing of Pravastatin Sodium by Addition of the Organic Base

Example 8
Stabilizing by Addition of L-Arginine

Pravastatin Sodium (I-17226103B, 5 g) with chromatographic purity 99.5% and pH 7.4 (1%)/7.7 (5%) was dissolved in methanol (30 ml), L-arginine (10 mg, dissolved in 0.15 ml of water) was added and finally, ethylacetate (400 ml, containing 2% of water) was added. After 1 hour the resulted crystals were filtered off, washed with fresh ethylacetate (50 ml) and dried at 40° C. for 6 hours in vacuo.

The chromatographic purity of resulted crystals (4.3 g) was 99.6% and pH was 8.9 (1%)/9.3 (5%).

The results of the stability measurements are shown in Table 1.

(VI) Results of Examples 1 to 8

TABLE 1

Results of Examples 1 to 8

| Sample | Experiment Buffer/ basifying substance | After preparing Value pH (1%) | After preparing Value pH (5%) | After 1 week on air atm Value pH (1%) | After 1 week on air atm Value pH (5%) |
|---|---|---|---|---|---|
| Reference example Raw crystals of pravastatin I-17226103 B | — | 7.4 | 7.7 | 7.2 | 7.6 |
| Ex 1 | Na2CO3 | 9.5 | 9.8 | 9.5 | 9.8 |
| Ex 2 | NaHCO3 | 9.2 | 9.6 | 9.3 | 9.7 |
| Ex 3 | Na2HPO4 | 8.0 | 8.4 | 8.0 | 8.4 |
| Ex 4 | NaOH/CO2 | 7.7 | 8.3 | 7.7 | 8.4 |
| Ex 5 | Aminoguan. HCO3 | 8.1 | 8.8 | 8.2 | 8.9 |
| Ex 6 | CH3COONa | 7.9 | 8.3 | 8.0 | 8.4 |
| Ex 7 | MgO | 8.7 | 9.3 | 8.8 | 9.5 |
| Ex 8 | L-arginine | 8.9 | 9.3 | 8.9 | 9.3 |

(VII) Stabilizing of Pravastatin Sodium by Addition of Salts of Organic Acids with Basic Character

Example 9
Stabilizing of Pravastatin Sodium by Addition of 3-(N-Morpholino) propanesulfonic acid (MOPS) Sodium Salt Pravastatin Sodium (I-17226103B, 5 g) with chromatographic purity 99.5% and pH 7.4 (1%)/7.7 (5%) was dissolved in methanol (30 ml), 3-(N-Morpholino) propanesulfonic acid Sodium salt (50 mg, dissolved in 0.3 ml of water) was added and finally, ethylacetate (400 ml containing 2% of water) was added. After 1 hour the resulted crystals were filtered off, washed with fresh ethylacetate (50 ml) and dried at 40° C. for 6 hours in vacuum.

The chromatographic purity of resulted crystals (4.3 g) was 99.5% and pH was 8.1 (1%)/8.5 (5%).

(VIII) Stabilizing of Pravastatin Sodium by Addition of the Organic Base

Example 10
Stabilizing by Addition of Tris(Hydroxymethyl) Aminomethane

Pravastatin Sodium (I-17226103B, 5 g) with chromatographic purity 99.5% and pH 7.4 (1%)/7.7 (5%) was dissolved in methanol (30 ml), tris(hydroxymethyl) aminomethane (50 mg, dissolved in 0.4 ml of water) was added and finally, ethylacetate (400 ml, containing 2% of water) was added.

After 1 hour the resulted crystals were filtered off, washed with fresh ethylacetate (50 ml) and dried at 40° C. for 6 hours in vacuum.

The chromatographic purity of resulted crystals (4.3 g) was 99.6% and pH was 8.0 (1%)/8.3 (5%).

Example 11

Stabilizing by Addition of N,N1-bis(2-hydroxyethyl) ethylenediamine

Pravastatin Sodium (I-17226103B, 5 g) with chromatographic purity 99.5% and pH 7.4 (1%)/7.7 (5%) was dissolved in methanol (30 ml), N,N1-bis(2-hydroxyethyl) ethylenediamine (50 mg, dissolved in 0.4 ml of water) was added and finally, ethylacetate (400 ml, containing 2% of water) was added. After 1 hour the resulted crystals were filtered off, washed with fresh ethylacetate (50 ml) and dried at 40° C. for 6 hours in vacuum.

The chromatographic purity of resulted crystals (4.3 g) was 99.6% and pH was 8.3 (1%)/8.9 (5%).

(IX) Results of Examples 9 to 11

TABLE 2

Results of Examples 9 to 11

| Experiment | | After preparing Value pH | | After 1 week in air atmosphere Value pH | |
|---|---|---|---|---|---|
| Sample | Buffering/ basifying agent | 1% solution | 5% solution | 1% solution | 5% solution |
| Reference example Raw crystals of sodium pravastatin | — | 7.4 | 7.7 | 7.2 | 7.6 |
| Ex 9 | MOPS Sodium salt | 8.1 | 8.5 | 8.1 | 8.6 |
| Ex 10 | Tris (hydroxymethyl) aminoethane | 8.0 | 8.3 | 8.0 | 8.3 |
| Ex 11 | N,N'-bis (2-hydroxyethyl) ethylenediamine | 8.3 | 8.9 | 8.3 | 8.8 |

(X) Evaluation

The main cause for the instability of the active substance HMG-CoA reductase inhibitor in bulk, such as pravastatin sodium, is carbon dioxide from the air and the consecutive lowering of the pH of the active substance. The result of lowering of the pH is conversion of pravastatin sodium into the lactone form.

Using various buffers or basifying agents in co-precipitation and/or co-crystallization with the active substance HMG-CoA reductase inhibitor, it is possible to make a very homogeneous composition as the pharmaceutically active substance where the HMG-CoA reductase inhibitor is effectively protected from being destabilized, see the results shown in Tables 1, 2 and 3. At the same time, the pH of bulk active substance may be set to an appropriate value as desired. For example, pravastatin sodium is stable especially at a pH of between 8 and 10.

In the above examples 0.2 w/w % of buffering or basifying agent realtive to pravastatin sodium was used, but lower or higher amounts also work effectively.

The compositions according to the present invention obtained as described above can be incorporated in typical amounts into the pharmaceutical formulation, for example as described in the earlier PCT application No. PCT/IB99/01749 (publication No. WO 00/35425) incorporated herein by reference, where the active substance is replaced by the compositions according to the present invention.

What is claimed is:

1. A composition comprising a homogeneous mixture of a HMG CoA reductase inhibitor with a buffering substance or a basifying substance in a finely distributed form, obtained by co-crystallization and/or co-precipitation of said HMG CoA reductase inhibitor and said buffering substance or basifying substance, which has a HPLC purity of at least 98%.

2. A composition according to claim 1 which has a HPLC purity of at least 99.5%.

3. A composition according to claim 1 which has a HPLC purity of 99.6%.

4. A composition according to claim 1 which has a pH value in the range from 7 to 12.

5. A composition according to claim 1 which has a pH value in the range from 8 to 11.

6. A composition according to claim 1 wherein the said HMG CoA reductase inhibitor is selected from the group consisting of pravastatin, atorvastatin, fluvastatin, cerivastatin and pharmaceutically acceptable salts thereof.

7. A composition according to claim 1 wherein the said HMG CoA reductase inhibitor is a sodium salt of pravastatin, or a calcium salt of atorvastatin.

8. A composition according to claim 1, wherein the said HMG CoA reductase inhibitor is a sodium salt of pravastatin.

9. A composition according to claim 1, wherein the said HMG CoA reductase inhibitor is a calcium salt of atorvastatin (atorvastatin Ca).

10. A composition comprising a homogeneous mixture of a HMC CoA reductase inhibitor with a buffering substance or a basifying substance in a finely distributed form, obtained by co-crystallization and/or co-precipitation of said HMG CoA reductase inhibitor and said buffering substance or basifying substance and containing less than 0.5% wt of lactone form of the said HMG CoA reductase inhibitor.

11. A composition according to claim 10, wherein the content of the lactone form of the said HMG CoA reductase inhibitor is below 0.2% wt.

12. A composition according to claim 10, wherein the content of the lactone form of the said HMG CoA reductase inhibitor is below 0.1% wt.

13. A composition according to claim 10, wherein the content of the lactone form of the said HMG CoA reductase inhibitor is below 0.06% wt.

14. A composition according to claim 10, wherein the content of the lactone form of the said HMG CoA reductase inhibitor is below 0.05% wt.

15. A composition according to claim 10, wherein the content of the lactone form of the said HMG CoA reductase inhibitor is below 0.01% wt.

16. A composition according to claim 10, wherein the content of the lactone form of the said HMG CoA reductase inhibitor does not change significantly under the storage and/or handling conditions.

17. A composition according to claim 10, wherein the content of the lactone form of the said HMG CoA reductase inhibitor does not change significantly under the storage and/or handling conditions and is and/or remains below 0.5% wt.

18. A composition according to claim 10, wherein the content of the lactone form of the said HMG CoA reductase inhibitor does not change significantly under the storage and/or handling conditions and is and/or remains below 0.2% wt.

19. A composition according to claim 10, wherein the content of the lactone form of the said HMG CoA reductase inhibitor does not change significantly under the storage and/or handling conditions and is and/or remains below 0.1% wt.

20. A composition according to claim 10, wherein the content of the lactone form of the said HMG CoA reductase inhibitor does not change significantly under the storage and/or handling conditions and is and/or remains below 0.01% wt.

21. A composition according to claim 10, wherein the content of the lactone form of the said HMG CoA reductase inhibitor does not change significantly under the storage and/or handling conditions and is and/or remains below 0.06% wt.

22. A composition according to claim 10, wherein the content of the lactone form of the said HMG CoA reductase inhibitor does not change significantly under the normal storage and/or handling conditions.

23. A composition according to claim 10, wherein the content of the lactone form of the said HMG CoA reductase inhibitor does not change significantly under the normal storage and/or handling conditions and is and/or remains below 0.5% wt.

24. A composition according to claim 10, wherein the content of the lactone form of the said HMG CoA reductase inhibitor does not change significantly under the normal storage and/or handling conditions and is and/or remains below 0.2% wt.

25. A composition according to claim 10, wherein the content of the lactone form of the said HMG CoA reductase inhibitor does not change significantly under the normal storage and/or handling conditions and is and/or remains below 0.1% wt.

26. A composition according to claim 10, wherein the content of the lactone form of the said HMG CoA reductase inhibitor does not change significantly under the normal storage and/or handling conditions and is and/or remains below 0.06% wt.

27. A composition according to claim 10, wherein the content of the lactone form of the said HMG CoA reductase inhibitor does not change significantly under the normal storage and/or handling conditions and is and/or remains below 0.05% wt.

28. A composition according to claim 10, wherein the content of the lactone form of the said HMG CoA reductase inhibitor does not change significantly under the normal storage and/or handling conditions and is and/or remains below 0.01% wt.

29. A composition according to claim 10, wherein the content of the lactone form of the said HMG CoA reductase inhibitor does not change significantly under the stress storage conditions.

30. A composition according to claim 10, wherein the content of the lactone form of the said HMG CoA reductase inhibitor does not change significantly under the stress storage conditions and is and/or remains below 0.5% wt.

31. A composition according to claim 10, wherein the content of the lactone form of the said HMG CoA reductase inhibitor does not change significantly under the stress storage conditions and is and/or remains below 0.2% wt.

32. A composition according to claim 10, wherein the content of the lactone form of the said HMG CoA reductase inhibitor does not change significantly under the stress storage conditions and is and/or remains below 0.1% wt.

33. A composition according to claim 10, wherein the content of the lactone form of the said HMG CoA reductase inhibitor does not change significantly under the stress storage conditions and is and/or remains below 0.6% wt.

34. A composition according to claim 10, wherein a pH value of the composition in an aqueous solution or an aqueous dispersion is in the range from 7 to 12.

35. A composition according to claim 10, wherein a pH value of the composition in an aqueous solution or an aqueous dispersion is in the range from 8 to 11.

36. A composition according to claim 10, wherein a PH value of the composition in an aqueous solution or an aqueous dispersion does not change significantly when the said composition is stored and/or handled under the storage and/or handling conditions.

37. A composition according to claim 10, wherein a pH value of the composition in an aqueous solution or an aqueous dispersion does not change significantly when the said composition is stored and/or handled under the storage and/or handling conditions and remains in the range of pH from 7 to 12.

38. A composition according to claim 10, wherein a pH value of the composition in an aqueous solution or an aqueous dispersion does not change significantly when the said composition is stored and/or handled under the normal storage and/or handling conditions.

39. A composition according to claim 10, wherein a pH value of the composition in an aqueous solution or an aqueous dispersion does not change significantly when the said composition is stored under the stress storage conditions.

40. A composition according to claim 10, wherein the said HMG CoA reductase inhibitor is selected from the group consisting of pravastatin, atorvastatin, fluvastatin, cerivastatin and pharmaceutically acceptable salts thereof.

41. A composition according to claim 10, wherein the said HMG CoA reductase inhibitor is a sodium salt of pravastatin or a calcium salt of atrovastatin.

42. A composition according to claim 10, wherein the said HMG CoA reductase inhibitor is a sodium salt of pravastatin.

43. A composition according to claim 10, wherein the said HMG CoA reductase inhibitor is a calcium salt of atorvastatin.

* * * * *